United States Patent
Andersson

[11] Patent Number: 5,107,826
[45] Date of Patent: * Apr. 28, 1992

[54] CORRECTIVE POSTURE DEVICE

[76] Inventor: Roland Andersson, Hantverkargatan 4, 722 12 Västerås, Sweden

[*] Notice: The portion of the term of this patent subsequent to Feb. 26, 2008 has been disclaimed.

[21] Appl. No.: 596,314

[22] Filed: Oct. 12, 1990

Related U.S. Application Data

[63] Continuation of Ser. No. 236,931, Aug. 26, 1988, Pat. No. 4,995,383.

[30] Foreign Application Priority Data

Aug. 27, 1987 [SE] Sweden .................... 8703313

[51] Int. Cl.⁵ .................... A61F 13/00; A61F 15/00
[52] U.S. Cl. .................... 602/19; 128/78; 606/213; 602/58
[58] Field of Search .................... 128/155, 157, 78; 606/213, 214, 215, 216

[56] References Cited

U.S. PATENT DOCUMENTS

| | | |
|---|---|---|
| 363,538 | 5/1887 | Penny . |
| 1,371,690 | 3/1921 | Kelly . |
| 2,273,873 | 2/1942 | Klein . |
| 2,646,040 | 7/1953 | Stanton . |
| 3,194,234 | 7/1965 | Duckman et al. . |
| 3,233,608 | 2/1966 | Scaler, Jr. . |
| 4,526,166 | 7/1985 | Silber . |
| 4,995,383 | 2/1991 | Andersson .................... 128/157 |

FOREIGN PATENT DOCUMENTS

| | | |
|---|---|---|
| 259349 | 5/1912 | Fed. Rep. of Germany . |
| 928389 | 11/1947 | France . |
| 2268504 | 11/1975 | France . |
| 1435853 | 5/1976 | United Kingdom . |
| 2123297 | 2/1984 | United Kingdom . |

OTHER PUBLICATIONS

"On Assessment of Shoulder Exercise And Load-Elicited Pain In The Cervical Spine", by Karin Harms-Ringdahl, Stockholm, Sweden, 1986, 1—page abstract.

*Primary Examiner*—David Isabella
*Assistant Examiner*—Paul Prebilic
*Attorney, Agent, or Firm*—Burns, Doane, Swecker & Mathis

[57] ABSTRACT

The present invention relates to a bandage which preferably has a greater length than width and which comprises a center part (1a) and bandage securing ends (1b, 1c) located on mutually opposite sides of the center part. Only the securing ends of the bandage are provided on one side thereof with an adhesive coating for securing the securing ends to an area of skin. One securing end (1c) is intended to be affixed to a skin area (2) in the lumbar region while the other securing end (1b) is intended to be affixed to a skin area (3) in the region of the lower or intermediate thoracic vertebrae. The length of the tape (1) between the securing ends (1b, 1c) when the back is straight and in the correct posture (FIG. 1) is slightly shorter than the distance between the aforementioned skin areas when measured via the small of the back (4). The center part (1a) is detachably attached to one or both securing ends (1b, 1c) by means of a velcro hook and loop attachment.

17 Claims, 1 Drawing Sheet

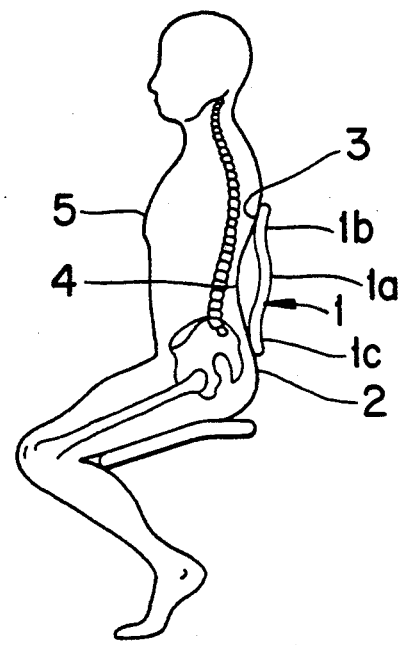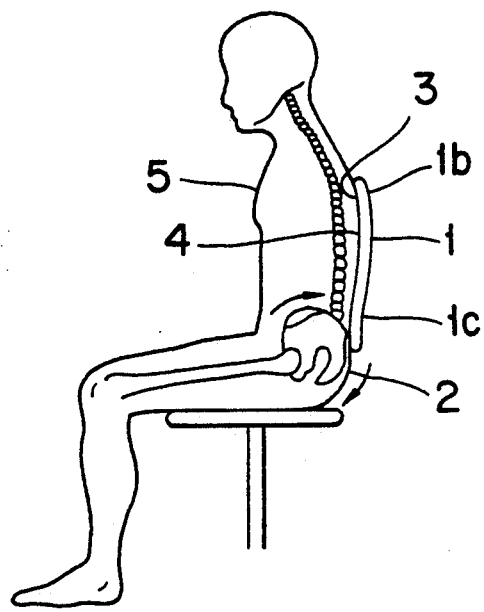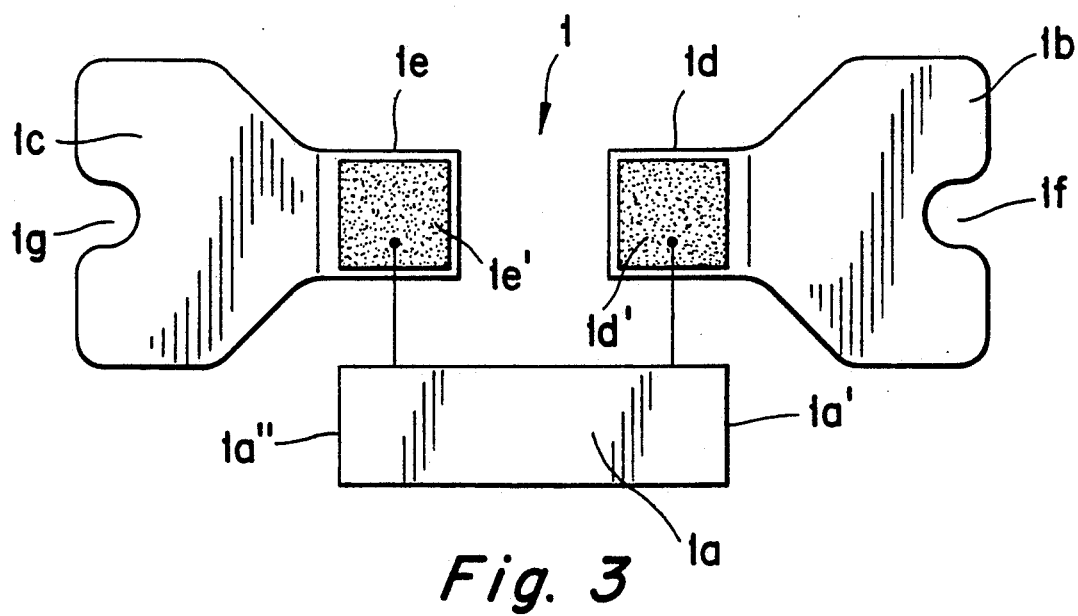

CORRECTIVE POSTURE DEVICE

This application is a continuation of application Ser. No. 07/236,931, filed Aug. 26, 1988 now U.S. Pat. No. 4,995,383.

BACKGROUND OF THE INVENTION

The present invention relates to a bandage, in particular to a bandage of the kind whose length exceeds its width.

1. Field of the Invention

The invention also relates to bandages of the kind which have a central portion and bandage securing ends located on mutually opposite sides of the central portion, the securing ends being coated with a layer of adhesive on one surface thereof.

A bandage which is devised in accordance with the present invention can be used as so-called fixation tape for treating patients who suffer with neck and back problems.

2. Description of the Related Art

Known to the art are a wide variety of plasters or bandages whose lengths exceed their respective widths and which have a central portion comprising gauze or a dressing and bandage securing ends which are located on mutually opposite sides of the central portion and which are coated with adhesive on one side thereof so that the bandage can be attached to the skin of the patient.

Examples of such known bandages are described and illustrated in U.S. Pat. Nos. 2,646,040 and 3,233,608.

Elastic bandages also form part of the relevant prior art.

The elastic bandage sold by Beiersdorf AG, Hamburg, West Germany under the trade name "ELASTOPLAST" can be mentioned as an example of such bandages, the elasticity of which is greater in their longitudinal directions than in their transverse directions and which have an adhesive coating on one side thereof.

Reference to an elastic part in the following description is intended to indicate a bandage section whose elasticity is the same as or similar to the elasticity of the aforesaid elastic bandage or tape in its longitudinal direction while reference to an inelastic part signifies a bandage section whose elasticity is the same as or similar to the elasticity of said bandage in its transverse direction.

The adhesive tape sold by 3M, U.S.A. under the trade name "DURAPORE" is also included here as an inelastic material which is coated with adhesive on one side thereof.

Complementary to the standpoint of technical background it can be mentioned that in the U.S. Pat. No. 3,194,234 there is disclosed a bandage having a trapezium-shaped centre part which incorporates pockets for accommodating metal stiffening elements and with elastic parts arranged on respective sides of the centre part.

SUMMARY OF THE INVENTION

An object of the present invention is to provide a "fixating tape" which is used as a corrective posture device attachable to the skin of a person's body for indicating when the person has an undesirable posture. The invention provides a fixating tape which creates conditions with simple means such that when applied to the skin of a person, the tape or bandage will not cause discomfort to the wearer when the part of the body to which the bandage is attached is bent within acceptable limits, but will give a gentle warning, in the form of slight discomfort, when this bending movement approaches unacceptable limits and creates pronounced discomfort when said movement exceeds said unacceptable limits, while still allowing the fixating tape or bandage to be adapted to suit different body forms.

In the case of bandages which are intended for use as fixating tapes in the treatment of neck and back ailments, a pronounced technical problem resides in the creation of conditions, with simple means, which will enable the adhesive-coated ends of the tape attached to the skin to take up the tensile forces which occur in said ends without the ends loosening or becoming displaced relative to the skin.

Another technical problem in the case of such fixating tape is one of obviating the need of strong adhesive coatings, since strong adhesives have an irritating effect on the skin of the wearer, at least in the case of persons with sensitive skin.

Another technical problem is one of providing conditions, with simple means, which will enable the use of a separate, narrow gauze central part and which will ensure that this central part will not break as a result of forces generated in the fixating tape in response to quick body movements, but will nevertheless have a sufficiently strong and readily removed attachment between said central part and respective bandage or tape securing ends.

A further technical problem resides in the provision of a tape or bandage with readily applicable fixation between its centre parts and respective securing ends and being adapted both for therapist and for patient.

Another technical problem resides in the provision of a fixating tape which will not be felt unduly by the patient when moving the body within acceptable limits.

This reduces the occurrence of the increased muscular activity, measurable by EMG-tests, which is experienced after a while by patients as a pronounced tiredness of the spine when a conventional tape is used.

A further technical problem is one of providing a bandage or tape with which the adhesive coatings on the bandage securing ends will not cause irritation of the skin and the occurrence of so-called tension blisters on the skin, even when the bandage is subjected momentarily to high tension forces.

A further technical problem resides in the provision of a single tape construction which can be adapted for use with different body forms and which affords a simple possibility of adjusting repeatedly the effect of the fixating tape.

Another technical problem resides in the provision of a simple fixating tape which will enable solely the central part to be removed (or loosened at one end) so as to enable the patient to rest, e.g. at night, without being subjected to the effect of the tape.

In the case of a single tape construction which can be adapted to different body forms another technical problem resides in the provision of conditions which will enable the effect produced by the tape to be adjusted by increasing or decreasing the length of the centre part between the points at which the tape is attached.

The present invention relates to a bandage, or tape, whose length preferably exceeds its width and which comprises a central part and securing ends located on mutually opposite sides of the central part, and with which one surface of respective ends is coated with an adhesive for securing the bandage to separate skin areas.

The invention is based on the assumption that one end of the tape or bandage is intended to be secured to the skin in the small of the back (the lumbar region) and the other end to the skin in the region of the lower or intermediate thoracic vertebrae.

The distance or length between the securing ends, with the centre part stretched slightly, shall be slightly smaller than the distance between the aforesaid skin areas via the curve of the back when the back is straight and held in the correct posture.

In accordance with the invention the centre part shall be attached to one or both of the securing ends in a manner which enables said part to be readily removed and attached.

In accordance with one embodiment, this ready removal and attachment of the centre part is effected with the aid of two mutually co-acting VELCRO hook and loop fastening tapes.

In this case, the two ends of the centre part are caused to extend slightly beyond their respective securing ends so as to form sufficiently extensive VELCRO hook and loop fastening surfaces.

As a result of this removable attachment facility, the longitudinal extension of the centre part between the separate securing ends can be varied easily, so that the bandage or tape can be adjusted to prevailing requirements.

It is also proposed that one part of a VELCRO hook and loop fastening attachment is attached to the two respective securing ends, and that the other part of the VELCRO hook and loop fastening attachment is attached to the aforesaid two end parts, said one part forming the so-called loop part and the securing ends carrying the "hook" parts of the "VELCRO" hook and loop fastening attachment.

Those advantages primarily afforded by the inventive bandage reside in the provision of possibilities which enable the bandage to be used as a fixating tape in the treatment of neck and back ailments and the securing ends of which are able to take up high tensile forces, and which enable the length extension of the centre part to be adjusted and therewith adapt the bandage readily to the varying body forms of different people and also allow different desired effects of the fixating tape to be obtained by one and the same person.

BRIEF DESCRIPTION OF THE DRAWINGS

A preferred embodiment of the inventive bandage used as a fixating tape will now be described with reference to the accompanying drawings in which FIG. 1 is a side view which illustrates the inventive bandage used as a fixating tape for maintaining a correct back or spine posture in the treatment of neck and back ailments;

FIG. 2 is a side view which shows the fixating tape when the back is sloped forwards, with the curve of the back fully straightened and tape stretched; and FIG. 3 shows the inventive fixating tape from above.

DETAILED DESCRIPTION OF THE PREFERRED EMBODIMENTS

FIG. 1 illustrates a bandage which has the form of a fixating tape or corrective posture device for treating patients suffering from neck and back ailments and the length of which exceeds its width. The bandage, or tape, is referenced 1 and has a centre part or member which can be in the form of a strap and securing ends 1b and 1c which can comprise two spaced-apart elements on mutually opposite sides of the centre part, the securing ends 1b and 1c having an adhesive coating on a first surface thereof.

The corrective posture device comprises means for providing discomfort to a person wearing the device when the person is in an undesirable posture. The means comprises body attachment means 1b, 1c for attaching the device to the person at two spaced-apart locations 2, 3 and adjustment means 1a for adjusting a distance that the device can be extended without providing discomfort to the person wearing the device. The attachment means comprises adhesive for adhering the device to skin of the person's body at the two locations.

The adjustment means comprises a member 1a which is removable from the attachment means 1b, 1c and attachable to the attachment means 1b, 1c at two spaced-apart positions 2, 3 corresponding to the two locations of the body attachment means, the distance between the two positions being adjustable for purposes of setting a limit as to the amount of acceptable bending of a part of the body to which the device is attached.

The attachment means includes first fastening means 1d, 1e at the two locations 2, 3 for removably securing the member 1a to the attachment means and the member 1a includes second fastening means on the underside of member 1a cooperable with the first fastening means for removably securing the member to the attachment means. The attachment means comprises two spaced-apart elements 1b, 1c each of the elements having the adhesive on a first side thereof and the first fastening means on a second side thereof facing away from the first side. The adhesive can completely cover the first side of the two elements.

The first and second fastening means together comprise a VELCRO hook and loop fastening attachment. For instance, the first fastening means comprises a plurality of hook fasteners of a VELCRO hook and loop fastening attachment and the second fastening means comprises a plurality of loop fasteners of a "VELCRO" hook and loop fastening attachment.

Each of the elements includes a first section and a second section which are coplanar with each other, the second section having a planar cross-sectional area which is smaller than a planar cross-sectional area of the first section. The first fastening means 1d, 1e can be provided only on the second section of the elements 1b, 1c. The first section of at least one of the elements includes a cut-out 1f, 1g therein and the adhesive can cover an area of the first side of the first section located in close proximity to the cut-out. The cut-out 1f, 1g extends inwardly from an edge of the first section which faces away from the second section.

The adhesive coating on the securing end 1c is intended to secure said end to a skin area 2 in the lumbar region, while the adhesive coating on the securing end 1b is intended to secure said end to a skin area 3 in the region of the lower or intermediate thoracic vertebrae.

It will be seen from FIG. 1 that the tape shall be applied so that when the back is straight (FIG. 1) the length of the tape between the securing ends 1b and 1c is slightly shorter than the shortest distance between the skin areas 2 and 3 via the small of the back 4, which is illustrated in FIG. 1 by showing the tape arched slightly to the right as seen in the Figure. The tape is thus not fully stretched between the skin areas 2 and 3 when securing the tape with the back correctly positioned.

FIG. 2 illustrates stretching or tightening of the tape when the back is bent forwards into an undesirable posture, while straightening the curve of the back.

When the back is held in a non-detrimental posture or position, the patient will not feel the tape, whereas when the back is moved towards a detrimental posture the patient will suffer discomfort from the tape. When the back is moved into a position which is fully detrimental to the patient, the tape will stretch to an extent which causes acute discomfort, these feelings of discomfort varying more or less proportionally with the extent of deviation from the correct back posture.

In accordance with the invention the bandage, or tape, will have located between at least one securing end and the centre part a further part 1d and 1e which will enable the centre part to be removed easily but which is also effective in firmly holding said centre part.

The fixating tape is shown from above in FIG. 3, from which it will be seen that the centre part of this embodiment is narrower than the securing ends and that the further parts 1d and 1c have a taper which faces the centre part 1a.

The securing ends 1b, 1c have a cut-out or like recess 1f and 1g respectively at the ends thereof remote from the centre part 1a.

It is proposed that the centre part 1a is totally inelastic in both the longitudinal and transverse directions.

Each of the securing ends is coated on one side thereof with a layer of adhesive which is kind to the skin and which has been allergy tested and which will adhere strongly to the skin of a patient.

It is also proposed that the central part 1a and the two further parts 1d and 1e are free from such adhesive coatings.

It is further proposed in accordance with the invention that the bandage is made from a synthetic, tear resistant non woven fabric which will allow the skin to breath and which will dry quickly when becoming wet.

A particular advantage is afforded when the securing ends 1b, 1c are configured to afford the best possible adhesion against the skin and when the attachment surface is formed to produce the least possible irritation and wrinkling of the skin when the centre part 1a is subjected to loads which cause the occurrence of tensile forces between the skin and the securing or attachment part.

The fixating tape 1 illustrated in FIG. 3 comprises three parts i.e. a securing end 1b, a centre part 1a and a securing end 1c.

The centre part 1a shall be held firmly on, but readily removable from, the respective securing ends 1b and 1c, and to this end an "loop part" 1d' and 1e' of a VELCRO hook and loop fastening connection is attached to the part 1d and 1e, where the "hook part" is applied to the end parts 1a' and 1a" of the centre part 1a.

This enables the length of the centre part 1a between the securing ends 1b and 1c to be easily adjusted, or the centre part to be removed completely, if desired.

The VELCRO hook and loop fastening connection can be either woven into, sewn on, or welded to respective parts 1b and 1c, or affixed thereto in some other suitable manner such as with glue.

It will be apparent from FIG. 3 that the length of the centre part 1a shall be such that a portion of the centre part will cover the parts 1d and 1e so as to afford full co-action between the centre part and the securing ends or the attachment points.

It will be understood that the illustrated and described embodiment does not limit the invention and that modifications can be made within the scope of the following claims.

I claim:

1. A method for warning a person when that person has an undesirable posture of the pelvis and/or spinal column, said method comprising the steps of:
   securing first and second attachment means to first and second locations, respectively, on a skin part of said person's back;
   positioning said pelvis and/or said spinal column of said person into a desirable posture; and
   when said person is assuming the desirable posture, interconnecting said first and second attachment means with means for limiting the distance between said first and second attachment means such that when the pelvis and/or spinal column of said person is bent to a preselected limit, a discomfort is experienced by the person.

2. The method of claim 1, wherein the first location is the lumbar area and the second location is the lower or intermediate thoracic vertebrae of the person.

3. The method of claim 1, wherein the securing step comprises attaching the attachment means with an adhesive.

4. The method of claim 1, wherein the interconnecting step further comprises adjusting the limiting means so that when the pelvis and/or spinal column of the body is bent beyond the preselected limit, a pronounced discomfort is experienced by the person.

5. A corrective posture device attachable to a person's body for indicating to a person wearing the device when that person has an undesirable back posture, said device being large enough to extend between the lumbosacral region of the back and the region of the lower or intermediate thoracic vertebrae comprising:
   means for providing discomfort to a person wearing said device when the person has an undesirable back posture, said means comprising body attachment means for attaching said device to the person at two spaced-apart locations and adjustment means having a length sufficient to extend between said lumbosacral region and said lower or intermediate thoracic vertebrae for adjusting a distance said device can be extended without providing discomfort to the person wearing the device, said attachment means including adhesive adhering said device to skin of the person's body at said two locations, the adhesive providing the discomfort by pulling on the person's skin when the adjusting means is extended, said adjustment means comprising a member which is removably attached to said attachment means at two spaced-apart positions on said member corresponding to said two locations, a distance between said two positions being variable for purposes of fitting the device to the person wearing the device, said attachment means including first fastening means at said two locations for removably securing said member to said attachment means and said member including second fastening means cooperable with said first fastening means for removably securing said member to said attachment means, said first fastening means comprising a plurality of hook fasteners and said second fastening means comprising a plurality of loop fasteners.

6. The device of claim 5, wherein said attachment means comprises two discrete spaced-apart elements, each of said elements having said adhesive on a first side thereof and said first fastening means on a second side thereof facing away from said first side, said elements being configured to afford maximum adhesion against the skin and an attachment surface of each of the said elements being formed to produce minimum irritation and wrinkling of the skin when the member is subjected to loads which cause occurrence of tensile forces between the skin and the attachment surfaces of the elements.

7. The device of claim 6, wherein said adhesive completely covers said first side of said two elements.

8. The device of claim 6, wherein each of said elements includes a first section and a second section, said second section having a planar cross-sectional area which is smaller than a planar cross-sectional area of said first section, said first and second sections being thin flat sections which are coextensive with each other.

9. The device of claim 8, wherein said first fastening means is provided only on said second section of said elements.

10. A corrective posture device attachable to a person's body for indicating to a person wearing the device when that person has an undesirable back posture, said device being large enough to extend between the lumbosacral region of the back and the region of the lower or intermediate thoracic vertebrae comprising:

means for providing discomfort to a person wearing said device when the person has an undesirable back posture, said means comprising body attachment means for attaching said device to the person at two spaced-apart locations and adjustment means having a length sufficient to extend between said lumbosacral region and said lower or intermediate thoracic vertebrae for adjusting a distance said device can be extended without providing discomfort to the person wearing the device, said attachment means including adhesive adhering said device to skin of the person's body at said two locations, the adhesive providing the discomfort by pulling on the person's skin when the adjusting means is extended, said adjustment means comprising a member which is removably attached to said attachment means at two spaced-apart positions on said member corresponding to said two locations, a distance between said two positions being variable for purposes of fitting the device to the person wearing the device, said attachment means including first fastening means at said two locations for removably securing said member to said attachment means and said member including second fastening means cooperable with said first fastening means for removably securing said member to said attachment means, said attachment means comprising two discrete spaced-apart elements, each of said elements having said adhesive on a first side thereof and said first fastening means on a second side thereof facing away from said first side, said elements being configured to afford maximum adhesion against the skin and an attachment surface of each of the said elements being formed to produce minimum irritation and wrinkling of the skin when the member is subjected to loads which cause occurrence of tensile forces between the skin and the attachment surfaces of the elements, each of said elements including a first section and a second section, said second section having a planar cross-sectional area which is smaller than a planar cross-sectional area of said first section, said first and second sections being thin flat sections which are coextensive with each other, said first section of at least one of said elements including a cut-out therein and said adhesive covering an area of said first side of said first section located in close proximity to said cut-out.

11. The device of claim 10, wherein said cut-out extends inwardly from an edge of said first section which faces away from said second section.

12. The device of claim 5, wherein said member is elongated and extends in a longitudinal direction and is substantially inelastic in said longitudinal direction and in a transverse direction which is perpendicular to said longitudinal direction.

13. The device of claim 8, wherein said first section is connected to said second section by a tapered section of each of said elements.

14. The device of claim 12, wherein said member is an elongated strap having a length greater than a width thereof, the width of the strap being less than a maximum width of each of said elements.

15. The device of claim 5, wherein said adjustment means comprises an elongated flat strap and said attachment means comprises a pair of flat elements, one side of said elements being coated with said adhesive for securing said elements to the skin of a person wearing the device, each of said elements having fastening means on only a portion thereof for releasably holding a respective end of said strap.

16. A corrective posture device attachable to a person's body for indicating to a person wearing the device when that person has an undesirable back posture, said device being large enough to extend between the lumbosacral region of the back and the region of the lower or intermediate thoracic vertebrae comprising:

means for providing discomfort to a person wearing said device when the person has an undesirable back posture, said means comprising body attachment means for attaching said device to the person at two spaced-apart locations and adjustment means having a length sufficient to extend between said lumbosacral region and said lower or intermediate thoracic vertebrae for adjusting a distance said device can be extended without providing discomfort to the person wearing the device, said attachment means including adhesive adhering said device to skin of the person's body at said two locations, the adhesive providing the discomfort by pulling on the person's skin when the adjusting means is extended, said adjustment means comprising an elongated flat strap and said attachment means comprising a pair of flat elements, one side of said elements being coated with said adhesive for securing said elements to the skin of a person wearing the device, each of said elements having fastening means on only a portion thereof for releasably holding a respective end of said strap, at least one of said elements including a cut-out in a portion thereof at which said fastening means is not located, said cut-out comprising a recess extending inwardly from an edge of said one element.

17. The device of claim 16, wherein said device includes two of said elements, each of said elements including a cut-out in a portion thereof at which said fastening means is not located, each of said cut-outs comprising a recess extending inwardly from one edge of the respective element.

* * * * *